United States Patent
Janeczek et al.

(10) Patent No.: US 10,704,553 B2
(45) Date of Patent: Jul. 7, 2020

(54) MAGNETIC COUPLING

(71) Applicant: TECHNISCHE UNIVERSITÄT WIEN, Vienna (AT)

(72) Inventors: Christoph Janeczek, Felixdorf (AT); Markus Hinteregger, Vienna (AT)

(73) Assignee: TECHNISCHE UNIVERSITÄT WIEN, Wien Österreich (AT)

( * ) Notice: Subject to any disclaimer, the term of this patent is extended or adjusted under 35 U.S.C. 154(b) by 442 days.

(21) Appl. No.: 15/311,300

(22) PCT Filed: May 13, 2015

(86) PCT No.: PCT/AT2015/050122
§ 371 (c)(1),
(2) Date: Nov. 15, 2016

(87) PCT Pub. No.: WO2015/172173
PCT Pub. Date: Nov. 19, 2015

(65) Prior Publication Data
US 2017/0080136 A1    Mar. 23, 2017

(30) Foreign Application Priority Data
May 15, 2014    (AT) .............................. A 50343/2014

(51) Int. Cl.
*F04D 13/06* (2006.01)
*H02K 49/10* (2006.01)
(Continued)

(52) U.S. Cl.
CPC ....... *F04D 13/0613* (2013.01); *A61M 1/1036* (2014.02); *A61M 1/12* (2013.01);
(Continued)

(58) Field of Classification Search
CPC ...... F04D 13/10; F04D 13/086; F04D 13/062; F04D 13/0613; F04D 13/0646;
(Continued)

(56) References Cited

U.S. PATENT DOCUMENTS 4,065,234 A * 12/1977 Yoshiyuki ............ H02K 49/108
310/103
5,292,284 A *  3/1994 Denk ................... H02K 49/106
310/104

(Continued)

FOREIGN PATENT DOCUMENTS

DE    11 2008 00285    1/2011
EP      0 039 777      11/1981
(Continued)

OTHER PUBLICATIONS

Austrian Office Action dated Mar. 27, 2015 issued in Austrian Patent Application No. A 50343/2014, 4 pp.
(Continued)

*Primary Examiner* — Kenneth J Hansen
(74) *Attorney, Agent, or Firm* — Nixon & Vanderhye P.C.

(57) ABSTRACT

Disclosed is a magnetic coupling for transmitting torque along an axis of rotation, comprising two coupling parts which can be rotated relative to each other, wherein a drive-side coupling part has a drive-side permanent magnet and wherein an output-side coupling part has an output-side permanent magnet that lies opposite and at a distance from the drive-side permanent magnet along the axis of rotation. One of the coupling parts comprises a diverting element which is at least partially ferromagnetic and is non-rotatably connected to the permanent magnet of said coupling part and one part of the diverting element is disposed radially outside the opposite permanent magnet.

17 Claims, 4 Drawing Sheets

(51) Int. Cl.
*A61M 1/10* (2006.01)
*A61M 1/12* (2006.01)
*H02K 7/00* (2006.01)
*F16D 27/01* (2006.01)

(52) U.S. Cl.
CPC ........... *H02K 7/003* (2013.01); *H02K 49/108* (2013.01); *F16D 27/01* (2013.01)

(58) Field of Classification Search
CPC ........ F04B 47/00; F04B 47/06; F04B 17/046; A61M 1/1036; H02N 13/00; F16D 27/004; F16D 27/01; F16D 27/04; F16D 27/14; F16D 2027/008; H02K 49/108; H02K 49/104; H02K 7/003
USPC .......................................................... 310/104
See application file for complete search history.

(56) References Cited

U.S. PATENT DOCUMENTS

| | | | | |
|---|---|---|---|---|
| 2003/0132003 | A1* | 7/2003 | Arauz | E21B 43/128 166/370 |
| 2006/0155158 | A1* | 7/2006 | Aboul-Hosn | A61M 1/12 600/16 |
| 2010/0259121 | A1* | 10/2010 | Ueda | F16D 27/01 310/103 |
| 2012/0046514 | A1* | 2/2012 | Bourque | A61M 1/101 600/16 |
| 2014/0077646 | A1 | 3/2014 | Osterberg | |

FOREIGN PATENT DOCUMENTS

| | | | |
|---|---|---|---|
| EP | 0 904 117 | 7/2000 | |
| WO | WO-2008127487 A1 * | 10/2008 | ............. H02K 49/10 |

OTHER PUBLICATIONS

International Search Report dated Nov. 6, 2015 issued in PCT International Patent Application No. PCT/AT2015/050122 and English Translation, 6 pp.
"Magnetic Coupling Delivers Increased Torque," NTIS Tech Notes, Oct. 1, 1989, p. 863.
Zheng, Pan et al., "Force and Torque Characteristics for Magnetically Driven Blood Pump," Journal of Magnetism and Magnetic Materials, vol. 241, No. 2-3, Mar. 1, 2002, pp. 292-302.
English Translation of International Preliminary Report on Patentability dated Nov. 24, 2016 issued in PCT International Patent Application No. PCT/AT2015/050122, 8 pp.

* cited by examiner

MAGNETIC COUPLING

This application is the U.S. national phase of International Application No. PCT/AT2015/050122 filed May 13, 2015 which designated the U.S. and claims priority to Austrian Patent Application No. A 50343/2014 filed May 15, 2014, the entire contents of each of which are hereby incorporated by reference.

The invention relates to a magnetic coupling for transmitting torque along an axis of rotation, comprising two coupling parts which can be rotated relative to each other, wherein a drive-side coupling part comprises a drive-side permanent magnet and wherein an output-side coupling part comprises an output-side permanent magnet that lies opposite and at a distance from the drive-side permanent magnet along the axis of rotation. More specifically, the invention relates to a compact magnetic coupling between separate functional areas without passing through a housing.

Substantially this design corresponds to the type of magnetic coupling generally known as disc coupling. A characteristic feature of this type of coupling is that the permanent magnets of the two coupling parts are axially adjacent and often arranged in a mirror-like fashion. Typically these two coupling parts are separated by an even separation plane which is perpendicular to the axis of rotation. A known alternative to this type of coupling is the concentric ring coupling, which comprises two coupling parts in the shape of hollow cylinders that are arranged coaxially inside one another. The basic structure of both types of couplings can be seen in EP 0 039 777 A2, for example. An advantage of concentric ring couplings is their better torque transmission, but with increasing miniaturisation manufacturing them is becoming difficult and cost-intensive because of the required thin-walled hollow cylindrical coupling parts and correspondingly flat permanent magnets. On the other hand, disc couplings with reduced design sizes exhibit a disproportional decline of the torque transmission, i. e. smaller dimensions of the coupling do not only reduce the available magnetised volume but also shorten the relevant radius for the transmitted torque.

A possible area of application for the magnetic coupling according to the invention in which small dimensions of the coupling are especially desirable is its use as an implantable medical device, in particular as a blood pump, preferably as a heart blood pump and/or heart catheter pump. Such a blood pump is already known from EP 0 904 117 B1, with the magnetic coupling shown therein designed as a disc coupling in a manner known per se between the drive and the pump rotor.

In contrast to the known types of construction the object of the invention is to propose a magnetic coupling which may be manufactured easier and more economical than comparable concentric ring couplings with predetermined, particularly compact dimensions while having increased efficiency with regard to the transmitted torque when compared to conventional disc couplings.

In a magnetic coupling of the initially mentioned type, this object is achieved according to the invention by one of the coupling parts comprising an at least partially ferromagnetic diverting element which is non-rotatably connected to the permanent magnet of the coupling part, wherein one part of the diverting element is disposed radially outside of the opposite permanent magnet. This diverting element may be shaped as a cup or a hollow cylinder comparable to the outer coupling part of a concentric ring coupling and may surround the respective other coupling part circumferentially, i. e. preferably it extends radially outside of both permanent magnets. The diverting element may be formed as a thin-walled hollow cylinder, for example, so that with unchanged dimensions the magnetised volume of the disc coupling is retained to the greatest possible extent and, at the same time, a transmittable torque comparable to that of a concentric ring coupling may be obtained between the diverting element and the opposite permanent magnet at a distance therefrom. The direction of magnetisation of the permanent magnets is preferably oriented perpendicular to the axis of rotation, i. e. the poles of the magnets extend circumferentially from south to north and are—at least in a two-pole design—diametrically opposite each other with respect to the axis of rotation. By means of the diverting element, magnetic field lines extending radially from the permanent magnets are bundled, and due to the ferromagnetic material of the diverting element the magnetic force between the coupling parts is further increased. The magnetic force for transmitting the torque is raised by compressing the magnetic field lines in the ferromagnetic material. Advantageously, due to the larger volumes of the permanent magnets when compared to concentric ring couplings with equal dimensions of the couplings, a shorter axial extension and thus lower radial transverse forces on the bearings of the coupling parts can be achieved.

A compact construction of the magnetic coupling having a comparably good torque-transmitting capability at the same time may be obtained by using 2-, 4- or 6-pole permanent magnets for each of the two permanent magnets. In order to optimise the transmitting capability of the magnetic couplings for the torque, the respective number of poles for both magnets is specified in particular depending on the diameter of the coupling. In comparably large magnetic couplings a higher number of poles is also possible. In case of the 2-pole design the permanent magnets may each comprise two half-cylindrical magnetic poles.

In order to avoid magnetic short circuits in the diverting element, the diverting element may comprise at least one diamagnetic separation parting the diverting element into at least two ferromagnetic sections. In case of a two-pole permanent magnet the separation may be formed as a diamagnetic dividing strip along a plane intersecting the permanent magnet centrally and transverse to the direction of magnetisation, i. e. the dividing strip parts the diverting element into two halves.

If the diverting element extends at a rear side of the non-rotatably connected permanent magnet which rear side is facing away from the opposite permanent magnet, the magnetisation of the diverting element and thus the transmitted torque can be further increased.

Moreover, it has proven favourable for the diverting element to comprise a hollow cylindrical jacket and preferably to be designed with an intermediate base arranged substantially at half height of the jacket. In this case, the diverting element comprises a substantially H-shaped longitudinal section with the intermediate base forming the cross web disposed perpendicular to the axis of rotation so that cup-shaped recesses are formed on both sides of the intermediate base. A permanent magnet is received and non-rotatably connected in one of these recesses.

A particularly high concentration of magnetic field lines within the diverting element may be achieved if a diamagnetic shielding element is arranged at a rear side of the permanent magnet non-rotatably connected to the diverting element which rear side is facing away from the opposite permanent magnet. In this way, field lines running outside of the coupling parts may be avoided, and thus losses related thereto may be reduced.

Furthermore, it has proven favourable if a diamagnetic shielding element is arranged at a front side of the permanent magnet non-rotatably connected to the diverting element which front side is facing the opposite permanent magnet, in particular in a region centred around the axis of rotation, which shielding element adjoins the diverting element preferably circumferentially or radially on the outside. Such a shielding makes it possible to divert the magnetic field to regions located at larger radial distances from the axis of rotation so the torque transmitted at a given magnetic force is increased.

For a torque transmission between separated functional areas, for example in pump applications having a pump rotor supported within the pumping medium, it is favourable for the two coupling parts to be hermetically separated. Such a hermetic separation may be obtained, for example, by a hermetic wall between the two coupling parts, which wall should be non-conductive both magnetically and electrically. It does not necessarily have to be part of a housing of the coupling, but may adjoin a housing, for example. Basically, however, the present magnetic coupling may also be used without any hermetic separation, for example in safety couplings, i. e. for limiting the transmitted torque.

In the context of a hermetic separation of the coupling parts it is advantageous if, in order to hermetically separate the two coupling parts, at least one of the coupling parts is accommodated in a substantially non-magnetic and electrically non-conductive housing. Such a housing makes it possible to avoid losses due to a reversal of magnetism of the housing and/or induced eddy currents in the housing.

The present magnetic coupling may be used especially advantageously in a pump having a drive and a pump rotor, with the pump rotor being connected to the drive via the magnetic coupling. The pump obtained in such a way may be designed particularly compact while transmitting a relatively high torque with a correspondingly advantageous pump output.

A type of use requiring particularly compact dimensions of the pump relates to implanted medical devices, in particular blood pumps, preferably heart blood pumps. A hermetic separation of drive and pump rotor is advantageous while a torque as high as possible is to be transmitted at the same time. The magnetic coupling proposed herein meets these requirements especially well.

The invention is explained in further detail below by means of particularly preferred exemplary embodiments, but without being limited to them, and with reference to the drawings. Individually, in the drawings.

Figure 1:
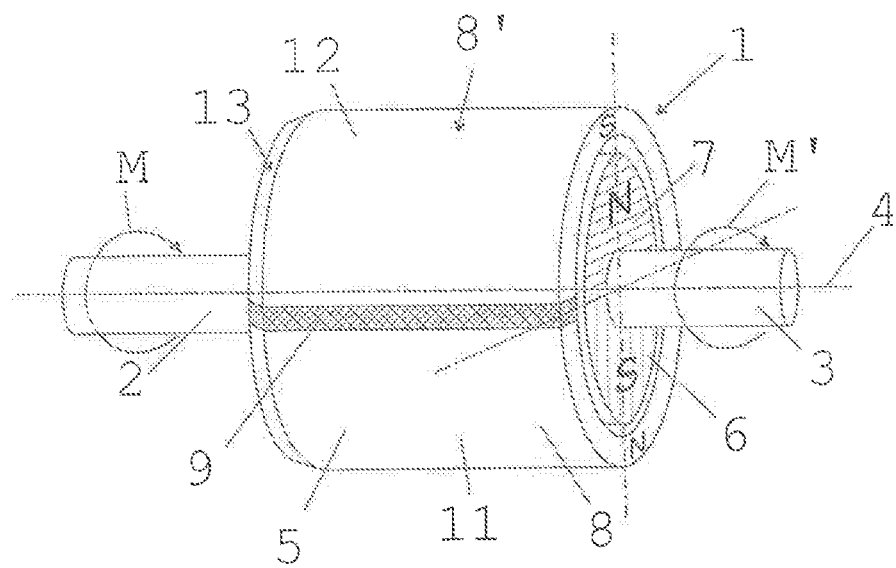
FIG. 1 shows a diagrammatic view of a magnetic coupling for transmitting a torque having a diverting element that is bevelled frustoconically at its rear side.

FIG. 1 illustrates a magnetic coupling 1, which connects a drive shaft 2 to an output shaft 3 for contact-free transmission of a torque M, M'. The two shafts 2, 3 are disposed on a common axis of rotation 4 so a drive-side coupling part 5 is rotatably supported relative to an output-side coupling part 6. The output-side coupling part 6 comprises an output-side two-pole permanent magnet 7, which is non-rotatably connected to the output shaft 3, in particular pushed onto the output shaft 3 (cf. FIG. 2). The output-side permanent magnet 7 is circumferentially surrounded by a substantially cup-shaped diverting element 8 having a hollow cylindrical jacket 8' and a disc-shaped, substantially flat base 8" that closes the jacket 8' on one end (cf. FIG. 2). Between the output-side permanent magnet 7 and the diverting element 8, a clearance or gap is provided so that the output-side coupling part 6 is coupled to the drive-side coupling part 5 in contact-free fashion. The diverting element 8 is mainly made of a ferromagnetic material. The jacket 8' of the diverting element 8 is only interrupted by a diamagnetic separation 9 in a narrow angular region, and furthermore, the separation 9 extends across the base 8". Substantially, the separation 9 parts the diverting element 8 into two ferromagnetic halves or half-shells. An intersecting plane running through the separation 9 is thus perpendicular to a direction of magnetisation of the drive-side two-pole permanent magnet 10 that is connected to the diverting element 8 (cf. FIG. 2). Consequently, the ferromagnetic sections 11, 12 of the diverting element 8 are magnetised in accordance with the drive-side permanent magnet 10. When using multi-pole permanent magnets 7, 10, appropriate additional separations are required within the diverting element 8 in order to allow an ideal magnetisation of the diverting element 8. The frustoconical bevel 13 at the drive side of the diverting element 8 permits to obtain a magnet field gradient as homogeneous as possible in the diverting element 8 and/or reduces possible losses of magnetisation caused by inhomogeneities at the edges.

Figure 2:
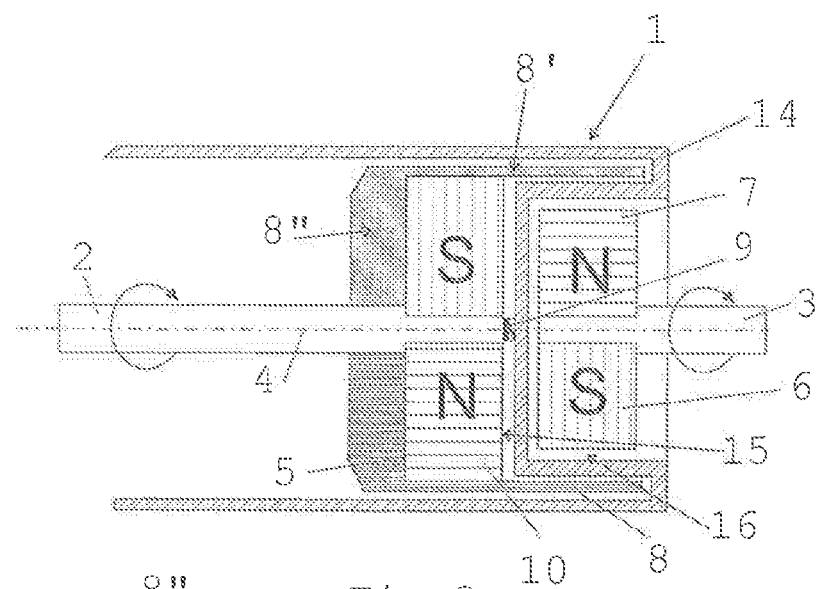
FIG. 2 shows a longitudinal section through a magnetic coupling according to FIG. 1, wherein the two coupling parts are separated by a housing.

FIG. 2 illustrates the magnetic coupling 1 shown in FIG. 1 in a longitudinal section, wherein the drive-side coupling part 5 is separated from the output-side coupling part 6 by means of a housing 14. Here, the housing 14 forms a hermetic separation between the functional areas of the two coupling parts 5, 6. The drive-side coupling part 5 having the drive-side permanent magnet 10 and the diverting element 8 is rotatably received within the housing 14, wherein the housing 14 continues along the cup-shaped recess in the diverting element 8 approximately to a front side 15 of the drive-side permanent magnet 10 and itself forms a correspondingly smaller cup-shaped recess 16 for receiving the output-side coupling element 6. Since the inner diameter of the jacket 8' of the diverting element 8 is naturally larger than the outer diameter of the opposite coupling part 6 rotatably arranged therein and/or its permanent magnet 7 and advantageously, at the same time, the permanent magnet 10 of the coupling part 5 connected to the diverting element 8 fills out the entire jacket 8' radially, its outer diameter is generally larger than that of the opposite permanent magnet 7. Thanks to the base 8" of the diverting element 8 made of a ferromagnetic material, field lines that might diverge to the rear side of the permanent magnet 10 are diverted to the front side via the diverting element 8 and thus contribute to the transmission of the torque. As can further be seen from FIG. 2, the two permanent magnets 7, 10 are pushed onto the respectively associated shafts 3, 2 and/or are penetrated by the shafts 3, 2 along the axis of rotation 4.

Figure 3:
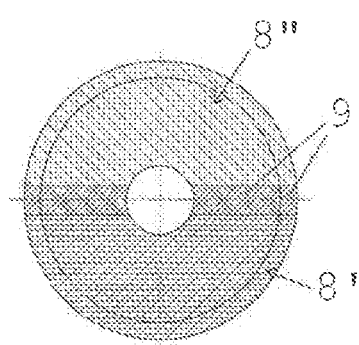
FIG. 3 shows a lateral view of a rear side of the drive-side coupling part according to FIG. 1 and FIG. 2, but without a housing.

FIG. 3 illustrates the magnetic coupling 1 viewed towards the base 8" of the diverting element 8, wherein the diamagnetic separation 9, which runs across the base 8" and parts the base 8" into two semicircular halves, can be seen.

Figure 4:
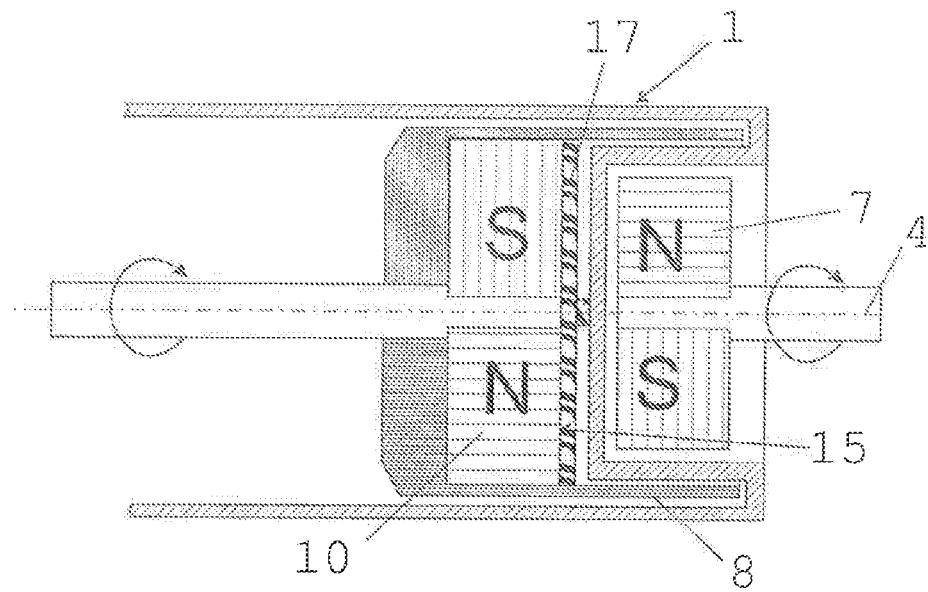
FIG. 4 shows a longitudinal section through an alternative embodiment of the magnetic coupling according to FIG. 2 having a diamagnetic shielding element at a front side of the drive-side coupling part.

FIG. 4 shows an extended alternative embodiment of the magnetic coupling 1 compared to FIG. 2, wherein the front side 15 of the permanent magnet 10 connected to the diverting element 8 is provided with a diamagnetic shielding element 17. The shielding element 17 counteracts a short circuit of the magnetic field lines between the two permanent magnets 7, 10 with small radii, i. e. near the axis of rotation 4. Here, the effective magnetic force is shifted towards larger radii, in particular to the diverting element 8, and thus a more efficient torque transmission is obtained.

Figure 5:
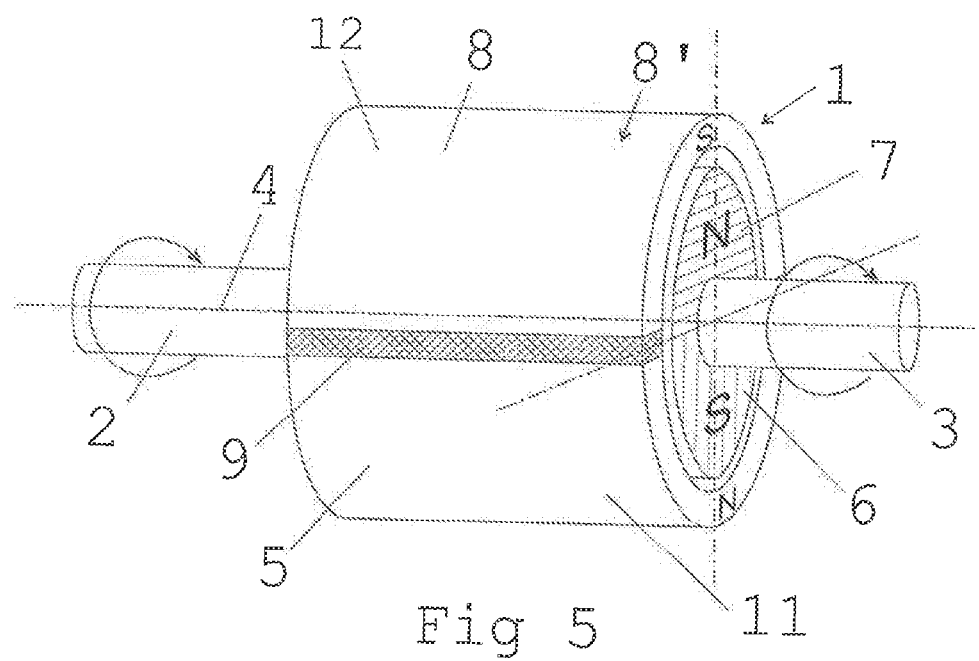
FIG. 5 shows a diagrammatic view of an alternative embodiment of a magnetic coupling for transmitting a torque having a diverting element without a frustoconical bevel of the diverting element at its rear side.

In the alternative embodiments of the magnetic coupling 1 described below, which correspond to the diagrammatic view shown in FIG. 5, no frustoconical bevel is provided at the rear side of the diverting element 8 in contrast to FIG. 1 due to constructional reasons. Apart from this, the basic design is identical to the magnetic coupling 1 shown in FIG. 1.

Figure 6:
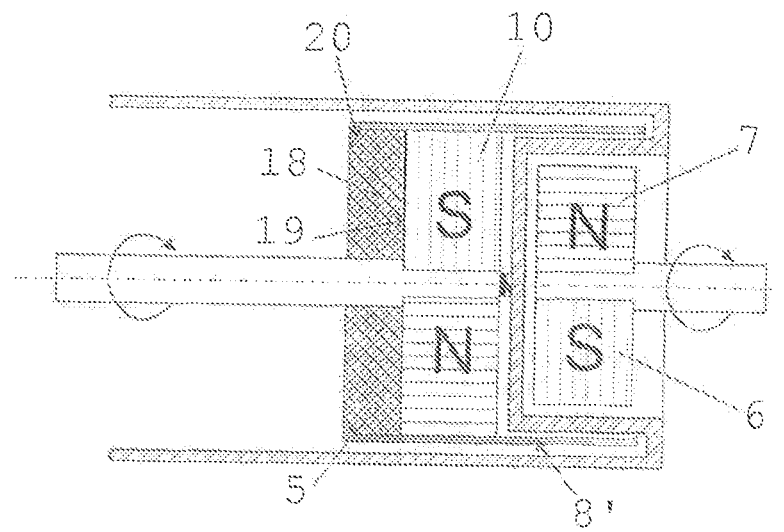
FIG. 6 shows a longitudinal section through a magnetic coupling according to FIG. 5, wherein the two coupling parts are separated by a housing, and with a diamagnetic shielding element at a rear side of the drive-side coupling part.
Figure 7:
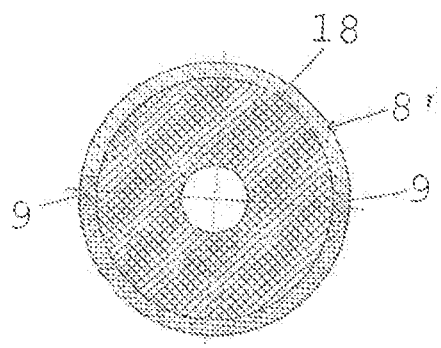
FIG. 7 shows a lateral view of a rear side of the drive-side coupling part according to FIG. 5 and FIG. 6 without a housing.

FIGS. 6 and 7 show an alternative embodiment of the magnetic coupling 1 in which the ferromagnetic base 8" of the diverting element 8 (cf. FIGS. 2 and 4) is replaced by a diamagnetic shielding element 18 at the rear side 19 of the permanent magnet 10 connected to the diverting element 8. By means of the shielding element 18, field lines of the permagnet field diverging to the rear side between the permanent magnets 7, 10 of the two coupling parts 5, 6 are avoided so that a correspondingly stronger magnet field is obtained at the outside and the front side. A separation 9 as with the ferromagnetic base 8" (cf. FIG. 3) is not required with the shielding element 18. For attaching the shielding element 18 in the diverting element 8, the jacket 8' of the diverting element 8 comprises a taper 20 at its closed end into which taper 20 the shielding element 18 is fitted. Consequently, the jacket 8' surrounds the permanent magnet 10 non-rotatably connected thereto and the opposite permanent magnet 7 as well as the shielding element 18.

Figure 8:
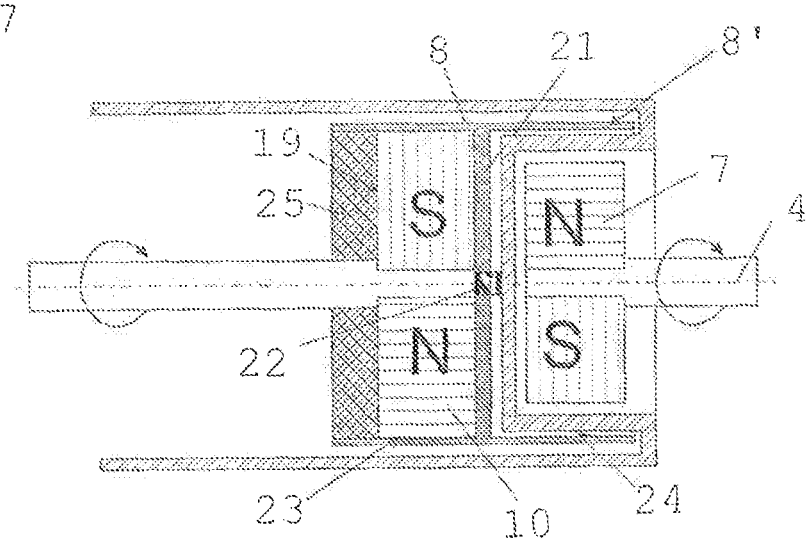
FIG. 8 shows a longitudinal section through a magnetic coupling according to FIG. 5, wherein the diverting element comprises an intermediate base, which is arranged at a front side of the drive-side coupling part, and with a diamagnetic shielding at its rear side.
Figure 9:
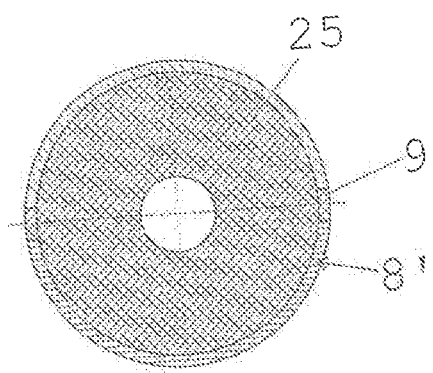
FIG. 9 shows a lateral view of a rear side of the drive-side coupling part according to FIG. 5 and FIG. 8 without a housing.

A further alternative embodiment of the magnetic coupling 1 is shown in FIGS. 8 and 9, wherein the diverting element 8 comprises an intermediate base 21 at about half height of the jacket 8' instead of the base 8". Like the base 8" (cf. FIG. 3), the intermediate base 21 comprises a dividing strip 22 running transversely through the axis of rotation 4. On both sides of the intermediate base 21 the diverting element 8 thus forms cup-shaped recesses 23, 24, wherein in the drive-side recess 23 the drive-side permanent magnet 10 is received and then a disc-shaped diamagnetic shielding element 25 is received and non-rotatably connected. Correspondingly, the output-side recess 24 surrounds the output-side permanent magnet 7. In contrast to the alternative embodiment of the magnetic coupling 1 shown in FIG. 6, the alternative embodiment according to FIG. 8 provides better dimensional stability of the diverting element 8 and thus higher mechanical durability of the magnetic coupling 1 with regard to manufacture.

Figure 10:
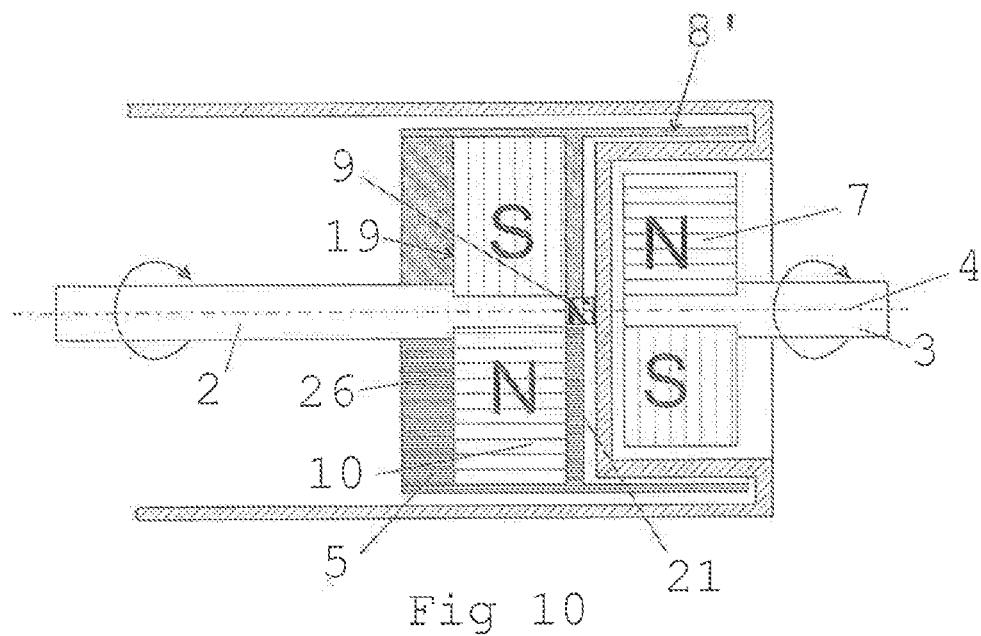
FIG. 10 shows a longitudinal section through a magnetic coupling according to FIG. 8, wherein the diamagnetic shielding is replaced by a ferromagnetic base.
Figure 11:
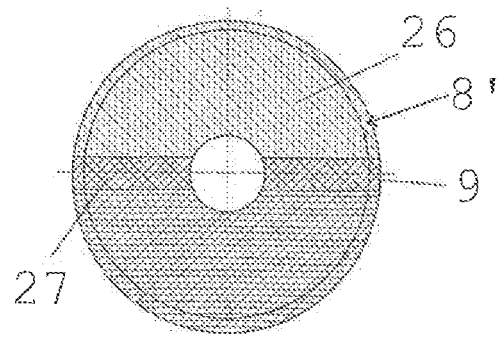
FIG. 11 shows a lateral view of a rear side of the drive-side coupling part according to FIG. 5 and FIG. 10 without a housing.

Substantially, the alternative embodiment of the magnetic coupling 1 shown in FIGS. 10 and 11 corresponds to the embodiment shown in FIGS. 8 and 9, but a ferromagnetic base 26 comparable to the base 8" of the diverting element 8 according to FIGS. 2 and 3 is inserted into the drive-side recess 23 instead of the diamagnetic shielding element 25. Favourably, the inserted base 26 also comprises a diamagnetic dividing strip 27 which parts the base 26 into two semicircular halves and thus avoids a short circuit of the magnetic circuit between the two poles of the permanent magnet 10 via the rear side of the coupling part 5.

The invention claimed is:

1. A magnetic coupling for transmitting torque along an axis of rotation, comprising two coupling parts which can be rotated relative to each other, one of the two coupling parts being a drive-side coupling part comprising a drive-side permanent magnet, and the other of the two coupling parts being an output-side coupling part comprising an output-side permanent magnet that lies, in a direction of the axis of rotation, opposite and at a distance from the drive-side permanent magnet, wherein the drive-side permanent magnet and the output-side permanent magnet are separated by an even separation plane which is perpendicular to the axis of rotation, wherein one of the two coupling parts comprises an at least partially ferromagnetic diverting element which is non-rotatably connected to one of the drive-side permanent magnet or the output-side permanent magnet of each permanent magnet's respective coupling part, and wherein one part of the diverting element is disposed radially outside the other of the drive-side permanent magnet or the output-side permanent magnet and wherein a direction of magnetisation of the drive-side permanent magnet and a direction of magnetisation of the output-side permanent magnet are oriented perpendicular to the axis of rotation.

2. The magnetic coupling according to claim 1, wherein the drive-side permanent magnet and the output-side permanent magnet are each 2-, 4- or 6-pole permanent magnets.

3. The magnetic coupling according to claim 1, wherein the diverting element comprises at least one diamagnetic separation parting the diverting element into at least two ferromagnetic sections.

4. The magnetic coupling according to claim 1, wherein the diverting element extends at a rear side of the one of the drive-side permanent magnet or the output-side permanent magnet, the rear side facing away from the other of the drive-side permanent magnet or the output-side permanent magnet.

5. The magnetic coupling according to claim 1, wherein the diverting element comprises a hollow cylindrical jacket.

6. The magnetic coupling according to claim 1, wherein a diamagnetic shielding element is arranged at a rear side of the permanent magnet connected to the diverting element, which rear side is facing away from the opposite permanent magnet.

7. The magnetic coupling according to claim 1, wherein a diamagnetic shielding element is arranged at a front side of the one of the drive-side permanent magnet or the output-side permanent magnet connected to the diverting element, which front side is facing the other one of the drive-side permanent magnet or the output-side permanent magnet.

8. The magnetic coupling according to claim 1, wherein the two coupling parts are hermetically separated.

9. The magnetic coupling according to claim 8, wherein in order to hermetically separate the two coupling parts, at least one of the coupling parts is accommodated in a substantially non-magnetic and electrically non-conductive housing.

10. A pump having a drive and a pump rotor, with the pump rotor being connected to the drive via the magnetic coupling according to claim 1.

11. A pump according to claim 10, wherein the pump is configured as a medical device.

12. The magnetic coupling according to claim 5, wherein the hollow cylindrical jacket is designed with an intermediate base arranged substantially at half height of the jacket.

13. The magnetic coupling according to claim 7, wherein the diamagnetic shielding element is arranged at the front side of the one of the drive-side permanent magnet or the output-side permanent magnet non-rotatably connected to the diverting element, which front side is facing the other of the drive-side permanent magnet or the output-side permanent magnet in a region centred around the axis of rotation.

14. A magnetic coupling for transmitting torque along an axis of rotation, comprising two coupling parts which can be rotated relative to each other, one of the two coupling parts being a drive-side coupling part comprising a drive-side permanent magnet, and the other of the two coupling parts being an output-side coupling part comprising an output-side permanent magnet that lies opposite and at a distance from the drive-side permanent magnet along the axis of rotation, wherein one of the two coupling parts comprises an at least partially ferromagnetic diverting element which is non-rotatably connected to the one of the drive-side permanent magnet or the output-side permanent magnet of each permanent magnet's respective coupling part, and wherein one part of the diverting element is disposed radially outside the other one of the drive-side permanent magnet or the output-side permanent magnet, wherein a diamagnetic shielding element is arranged at a front side of the one of the drive-side permanent magnet or the output-side permanent magnet non-rotatably connected to the diverting element, which front side is facing the other one of the drive-side permanent magnet or the output-side permanent magnet in a region centred around the axis of rotation, and wherein the shielding element adjoins the diverting element circumferentially.

15. The pump according to claim 11, wherein the medical device comprises an implantable blood pump.

16. The pump according to claim 15, wherein the implantable blood pump comprises a heart blood pump.

17. The pump according to claim 3, wherein the diamagnetic separation is formed as a diamagnetic dividing strip along a plane intersecting the one of the drive-side permanent magnet or the output-side permanent magnet centrally and transverse to the direction of magnetisation of the one of the drive-side permanent magnet or the output-side permanent magnet.

* * * * *